United States Patent [19]

Kleinerman

[11] 4,153,675

[45] * May 8, 1979

[54] IMMUNOFLUOROMETRIC METHOD AND APPARATUS FOR MEASURING MINUTE QUANTITIES OF ANTIGENS, ANTIBODIES AND OTHER SUBSTANCES

[76] Inventor: Marcos Kleinerman, S. Point Rd., Webster, Mass. 01550

[ * ] Notice: The portion of the term of this patent subsequent to Jul. 19, 1974, has been disclaimed.

[21] Appl. No.: 815,555

[22] Filed: Jul. 14, 1977

Related U.S. Application Data

[63] Continuation-in-part of Ser. No. 623,567, Oct. 20, 1975, Pat. No. 4,036,946.

[51] Int. Cl.² ............... G01N 21/52; G01N 33/16
[52] U.S. Cl. .................... 424/8; 23/230 B; 23/915; 250/458; 250/461 B; 195/103.5 A; 424/12; 422/56
[58] Field of Search ............ 23/230 B, 253 R, 259; 424/12; 250/365, 458, 461 B; 195/103.5 A; 424/8

[56] References Cited

U.S. PATENT DOCUMENTS

| | | | |
|---|---|---|---|
| 3,654,090 | 4/1972 | Schuurs | 195/103.5 A |
| 3,973,129 | 8/1976 | Blumberg | 23/230 B |
| 3,992,631 | 11/1976 | Harte | 250/365 |
| 4,036,946 | 7/1977 | Kleinerman | 424/12 X |

*Primary Examiner*—Sidney Marantz
*Attorney, Agent, or Firm*—Morse, Altman, Oates & Bello

[57] ABSTRACT

An apparatus for measuring minute quantities of antigens, antibodies and other substances characterized by binding reactions with one another for forming a sandwich constituting an inner layer having a distribution of an unlabelled reagent, an intermediate layer having a distribution of the substance to be measured and an outer layer having a distribution of a fluorescent labelled reagent, the labelled and unlabelled reagents having the same biochemical specificity. Illumination from an excitation source is directed towards the sandwich and the fluorescence emitted by the fluorescent label is detected for measuring minute quantities of the substance under diagnosis.

24 Claims, 3 Drawing Figures

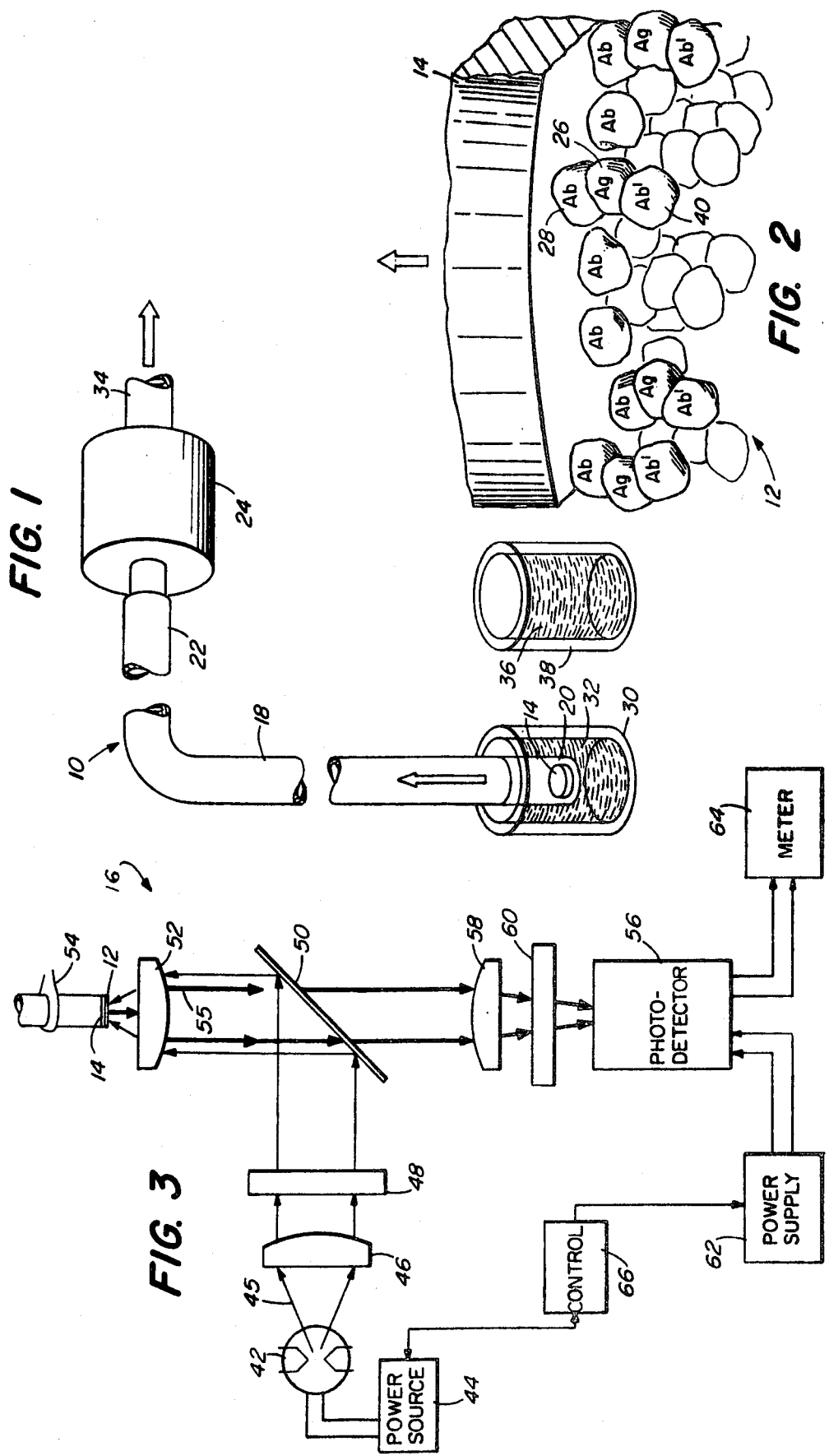

IMMUNOFLUOROMETRIC METHOD AND APPARATUS FOR MEASURING MINUTE QUANTITIES OF ANTIGENS, ANTIBODIES AND OTHER SUBSTANCES

CROSS-REFERENCE TO RELATED APPLICATIONS

The present application is a continuation-in-part of my pending application Ser. No. 623,567, filed Oct. 20, 1975, now U.S. Pat. No. 4,036,946.

BACKGROUND OF THE INVENTION

1. Field of Invention

The present invention relates to measuring methods and apparatuses and, more particularly, is directed towards methods and apparatuses for measuring minute quantities of antigens, antibodies, and other substances.

2. Description of the Prior Art

Methods for detecting and measuring antigens and antibodies are based on the very specific reactions between an antigen and its specific antibody. Often these reactions produce effects, like precipitation or agglutination, which are visible to the naked eye. Very often, however, a clinically significant concentration of the antigen (or antibody) is so small that visual methods are not applicable and sensitive instrumentation and methods are required for its determination. Presently, the most sensitive method is radioimmunoassay (RIA), which makes use of a specific antibody (or antigen) tagged with a radioactive tracer, whose concentration at the final stage of the appropriate procedure gives the concentration of the antigen (or antibody) originally present in the sample.

The radioactive tracer is typically Iodine 125, a gamma emitting isotope of Iodine. The gamma counters used for measuring the tagged reagent can detect down to about $10^{-10}$ g. of the antigen (or antibody), or typically $\geq 10^9$ antigen particles (or antibody molecules).

Two serious problems with RIA are long incubation times and the use of radioactive tagging agents with short half-lives. Long incubation times may lead to sample deterioration caused, for example, by the action of proteolytic enzymes present in human plasma. Radioactive tagging agents with short half-lives become unusable in a relatively short time, which increases the cost of the assays.

SUMMARY OF THE INVENTION

It is an object of the present invention to provide methods and apparatuses for measuring minute quantities of antigens, antibodies and other substances using relatively simple instrumentation, the sensitivity of such methods and apparatuses being comparable to that obtained in radioimmunoassay.

It is another object of the present invention to provide methods and apparatuses for measuring minute quantities of antigens, antibodies and other substances by forming a layered structure on a base stratum of small surface area. The layered structure includes an inner stratum of an unlabelled reagent that is attached to the base stratum, an intermediate stratum of a substance to be measured that is attached to the inner stratum, and an outer stratum of a fluorescent-labelled reagent or a reagent labelled with a fluorogenic substance that is attached to the intermediate stratum. Both the unlabelled reagent and the labelled reagent are characterized by a binding reaction with the substance to be measured. The resulting fluorescent structure is illuminated by an excitation source and the fluorescence is measured to provide an indication of the quantity of the substance to be measured.

The main feature of this invention is the concentration and immobilization of the substance to be measured on a surface area small enough to:

(a) increase the absorption of the light used for excitation of the fluorescent structure, thus increasing the fluorescence signal to a level suitable for adequate measurement;

(b) decrease the background fluorescent noise from the base stratum so as to further increase the signal-to-noise ratio; and (c) permit efficient optical coupling between the fluorescent structure and the excitation light source and between the fluorescent structure and the photodetector, thus further increasing the signal-to-noise ratio.

Other objects of the present invention will in part be obvious and will in part appear hereinafter.

The invention accordingly comprises the methods and devices, together with their steps and parts, elements and interrelationships, that are exemplified in the following disclosure, the scope of which will be indicated in the appended claims.

BRIEF DESCRIPTION OF THE DRAWINGS

A fuller understanding of the nature of the present invention will become apparent upon consideration of the following detailed description taken in connection with the accompanying drawings, wherein:

FIG. 1 is a perspective view of an apparatus for forming a layered structure on a base stratum in accordance with the present invention;

FIG. 2 is a schematic diagram illustrating certain principles of the invention; and FIG. 3 is a schematic diagram of a system embodying the invention for measuring minute quantities of a substance contained in the layered structure of FIG. 1.

DETAILED DESCRIPTION OF THE PREFERRED EMBODIMENTS

The present invention which includes fluorometric detection, is based on recent techniques for the immobilization of biopolymers, including antibodies and antigens (Lowe, C. R. and Dean, P. D. C. "Affinity Chromatography," Chapter IV. Wiley—1974). It is also based on known fluorescence antibody techniques and, in a variation of the method, on very recent techniques for tagging antibodies with enzymes, (Avrameas, S. Immunochemistry 8, page 1175, 1971).

Consider a chromographic column packed with a immobilized ligand (or antibody) L specific for a certain biopolymer (or antigen) P. A solution containing P is passed through the column and, as the P molecules (or antigen particles) collide with the L molecules they will be retarded, and an LP complex will be formed. If the interaction is strong (as is usually the case in antigen-antibody reactions) and the concentraction of L is high enough, P will become concentrated in a narrow zone at the top of the column.

Now, if the LP complex is tagged specifically by an fluorochrome F, then the concentration of P originally present in solution can be estimated from the fluorescence signal from F, obtained under suitable conditions. An in-column measurement would not be suitable for a low P concentration, since the geometry of the column is not conducive to either a high fluorescence excitation efficiency or a high fluorescence collection efficiency.

In the present invention, a relatively high concentration of LP is obtained on a thin, porous, solid support of small surface area containing a high concentration of immobilized ligand L. The process of concentrating P at this support should be essentially the same as the process of concentrating P at the top of the chromatographic column. After tagging with the fluorochrome F, the material on the support is efficiently illuminated with the fluorescence excitation radiation, as hereinafter described, and the fluorescence is efficiently collected.

Referring now to the drawings, FIG. 1 shows an apparatus 10 for forming a layered structure of the type generally shown in FIG. 2 at 12 on a base stratum 14 having a small surface area and FIG. 3 shows a system 16 for measuring minute quantities of a substance that is part of the layered structure. The substances forming layered structure 12, which is comprised of regular and/or irregular distributions of the substances, are characterized by binding reactions. The term surface area as used herein refers to a cross section of base stratum 14 and does not included the contribution from the microscopic structure of the base stratum. For example, the surface area of base stratum 14, shown in FIG. 2, refers to the cross section perpendicular to the direction of the arrow. The terms layered and layer as used herein are intended to include regular and/or irregular distributions of a substance or substances. In particular, layered structure 12 includes distribution of substances such as antigens and antibodies. An antigen is an agent that stimulates the formation of a corresponding antibody, the formed antibody reacting with the antigen. An antibody is a member of select class of serum proteins, referred to as immonoglobulins, which is formed as a reaction to an antigen and reacts with that specific antigen. In one example, an antibody is used to determine the presence and concentration of its specific antigen. In another example, an antigen is used to determine the presence and concentration of its specific antibody.

Apparatus 10 comprises a tublar member 18 having open ends 20 and 22. Base stratum 14, for example a porous disc containing the unlabelled reagent in a polymeric matrix, is snugly received within end 20 coaxial with tubular member 18. In the illustrated embodiment, the diameter of disc 14 is in the range of 0.1 mm to 10.0 mm and specifically is in the range of 0.5 mm to 5.0 mm. The thickness of disc 14 preferably is in the range of 0.05 mm to 2.0 mm and specifically is in the range of 0.1 mm to 0.5 mm. In the illustrated embodiment, the diameter and thickness of disc 14 is 2.0 mm and 0.2 mm, respectively. The inside diameter of tubular member 18, for example a glass tube, is such as to snugly receive disc 14. In an alternative embodiment base stratum 14 has a regular or irregular profile having a two-dimensional surface area in the range of $10^{-4}$ to $5 \times 10^{-1}$ cm$^2$. A suction device 24 is connected to end 22 of tube 18.

The method for forming layered structure 12 comprises the steps of immersing tubular member 18 and base stratum 14 into a fluid containing the substance to be analyzed. Next, forming an intermediate layer having a distribution of the substance to be analyzed by making the fluid flow through the base stratum, the substance to be analyzed attaching to a distribution of the unlabelled reagent which constitutes an inner layer. Next, preparing a solution containing a labelled reagent that bindlingly reacts with the substance to be analyzed, the labelled reagent having a fluorescent label. Then, immersing tubular member 18 and base stratum 14 into the solution, finally, forming layered structure 12 by making the solution flow through the intermediate layer, the third substance attaching to the substance to be analyzed and forming a final layer having a distribution of the labelled reagent. The number of molecules of the labelled reagent attached to the substance to be analyzed is determined by the number of particles of the substance to be analyzed that is attached to the unlabelled reagent. The number of labelled particles corresponds to the number of particles in the substance to be analyzed. The term particles as used herein describes a reacting unit of the substance to be analyzed and includes a single molecule as well as an aggregate of molecules.

In one example, the substance to be analyzed and measured is an antigen 26, the antigen particles are denoted as "Ag" in FIG. 2. Disc 14 is composed of a porous polymeric material such as porous glass coated with agarose in such a way that disc 14 remains porous to liquid flow. The diameter of disc 14 is 2.0 mm or less in order to (a) maximize the antigen concentration and, hence, that of the fluorescence tag, (b) achieve good collection efficiency of the fluorescence, and (c) minimize background fluorescence at the lower concentrations of antigen. The unlabelled reagent is an antibody 28, which reacts specifically with the antigen to be detected and measured, is attached covalently or by physical absorption, for example, to disc 14. The antibody particles are denoted as "Ab" in FIG. 2. Tube 18 is placed within a receptacle 30 containing a fluid 32 in which antigens 26 may be present. Suction device 24 is energized and fluid 32 flows from receptacle 30 through disc 14 and tube 18 and exits a discharge port 34. Antigen particles 26 in fluid 32 are trapped by the immobilized antibody particles on disc 14. Next, tube 18 is rinsed and is placed into a solution 36 containing the labelled reagent. Solution 36, which is contained in a receptacle 38, includes antibody molecules 28 that have a fluorescent label attached thereto, the labelled antibody molecules denoted by reference character 40 and "Ab'" in FIG. 2.

Suction device 24 draws solution 36 from receptacle 38 and passes it through disc 14. Labelled antibody molecules 40 attach themselves to the trapped antigen particles 26, thus forming layered structure 12. That is, apparatus 10 forms a layered structure comprising a first or inner layer having a distribution of unlabelled antibody molecules 28 that are immobilized on disc 12, an intermediate layer having a distribution of antigen particles 26 that are trapped by the immobilized antibody molecules, and a third or outer layer having a distribution of labelled antibody molecules that are attached to the trapped antigens. Disc 14 is utilized for measuring the antigen concentration of layered structure 12. In an alternate embodiment, other than a fluorescent tag is used, for example, a fluorogenic tag is used. A fluorogenic substance is defined herein as a substance which produces a fluorescent product after suitable treatment.

In another example, the labelled antibody instead of having a fluorescent tag, has an enzyme, like peroxidase, attached to it. The layered structure is formed in a similar manner as in the previous example. After washing off the unbound tagged antibody molecules, the surface containing the enzyme-tagged antibody is immersed in a solution containing an enzyme substrate which produces a fluorescent product, the concentration of which is dependent on the activity of the enzyme. Each tagged antibody will then produce a number n of fluorescent molecules, n being the enzyme amplification factor. The total number $N_t$ of fluorescent molecules thus produced can be orders of magnitude greater than the number of antigen particles trapped.

In one method for preparing a labelled antibody, a fluorescent molecule such as fluorescein is attached to an antibody molecule (a gamma-globulin) by reacting its isothiocynate derivative (fluorescein isothiocynate) with available amino ($NH_2$) groups in the gamma-globulin. The reaction product is an antibody molecule having a fluorescein molecule attached to it. The antibody thus labelled with the fluorescein molecule maintains its antibody specificity and is rendered fluorescent by exciting it with light that the fluorescein molecule absorbs. In an alternative embodiment, a fluorescent molecule other than fluorescein is attached to the antibody, for example, a fluorescent molecule such as N,N,N',N'-tetramethyl rhodamine is incorporated into an antibody molecule through its isothiocyanate derivative. The N,N,N',N'-tetramethyl rhodamine molecule is excited in the green region and emits in the red region. Fluorescein is excited in the blue region and emits in the green region. In the illustrated embodiment of system 16, in FIG. 3, antibody molecules 40 are labelled with N,N,N',N'-tetramethyl rhodamine.

In the examples mentioned, the substance to be measured was an antigen. The same procedure and apparatus is used to measure antibodies. When measuring antibodies, the immobilized reagent on the trapping matrix is an unlabelled antigen specific for the antibody to be measured. The labelled reagent is also an antigen specific for the antibody to be measured, and it is labelled by the same procedure described for labelling antibodies.

The same procedure and apparatus is used also for measuring any substance which can be trapped by an immobilized unlabelled reagent and tagged with a specific reagent having a fluoroscent or fluorogenic tag. Examples of such substances are hormones, serum proteins, serum macromolecules, subcellular particles, viruses, bacteria, whole cells and drugs.

Referring now to FIG. 3, it will be seen that system 16 comprises an excitation source 42 which is connected to a power supply 44. Excitation source 42, for example a mercury arc lamp such as an Osram HBO 100W/2 mercury lamp, generates a light beam 45 that is directed through a planoconvex lens 46 and a filter 48 towards a dichroic mirror or filter 50. In an alternative embodiment, source 42 is a laser, for example a red helium-neon laser. In the illustrated embodiment, by way of example, filter 48 is a mercury line filter that passes green light in the 546 nanometer mercury band. Dichroic filter 50 has a high reflectivity for the excitation radiation, for example green light, and has a high transmission for the fluorescence of the labelled antibody (or that of the product of the enzymatic reaction), for example red light. The light beam reflected by dichroic filter passes through a condensing lens 52 and is directed towards layered structure 12, tubular member 18 being captively held by a fastener 54, for example a clamp. That is, the excitation radiation from source 42 is collected and collimated by lens 46, filtered through filter 48 and directed to the surface containing the antigen sandwich (or to the solution containing the fluorescent product of the enzymatic reaction) through dichroic filter 50 and condensing lens 52. Labelled antibodies 40 are excited by the light directed thereto and emit red light 55 which is transmitted through dichroic filter 50. The transmitted light is directed towards a photodetector 56 via a planoconvex lens 58 and a barrier filter 60 which passes only red light, for example. Preferably, lens 45 and lens 52 have a large numerical aperture. Photodetecter 56, for example a photomultiplier tube which is powered by a high voltage supply 62, is coupled to a measuring device 64. Photomultiplier tube 56 generates a current that is proportional to the intensity of the light emitted by labelled antibody molecules 40. Measuring device 64, for example a dc ammeter or a photon counter measures the output signal generated by photomultiplier tube 56 and presents an indication of the presence and concentration of the labelled antibody molecules 40 which is directly related to the number of antigen molecules 26 in layered structure 12.

The small surface area of the trapping surface is dictated by the need to maximize the absorption of the excitation radiation by the fluorescent tag. A high surface density of immobilized antibodies is required for efficient trapping of the antigen particles. A surface density of $\geq 10^{12}$ immobilized antibody molecules per $cm^2$ may be attained, for instance, with a CNBr-treated polysacharide substrate, with the techniques developed by Porath's research group in Sweden-Porath, Axen, and Ernbäck, Nature, Vol. 215, page 1491, (1967).

The fluorescent signal generated by system 16, expressed in photoelectrons per second at the photocathode surface (before electron multiplication), is:

$$S = P (\lambda/hc) \cdot \alpha \cdot [\epsilon N] \cdot \phi \cdot \beta \cdot q$$

where:

P is the power in watts radiated by light source 42 in all directions, within the effective excitation band of the fluorescent label $\lambda$ is the excitation wavelength in cm h is Planck's constant in joule-sec-photon$^{-1}$ c is the velocity of light in cm-sec$^{-1}$ $\alpha$ is the fraction of P incident on the antigen-trapping surface $\epsilon$ is the absorbtion coefficient per labelled antibody molecule in $cm^2$-molecule$^{-1}$ N is the number of labelled antibody molecules per $cm^2$ of the illuminated field $\phi$ is the fluorescence quantum efficiency $\beta$ is the fraction of the emitted fluorescence which reaches the photocathode of photomultiplier tube 56 q is the photoelectric quantum efficiency of the photocathode in photoelectrons-photon$^{-1}$ In the following example, the fluorescent label is TRITC and is efficiently excited by the 546 nanometer mercury band. A short arc (0.3 mm), high pressure, 100 watt mercury arc (OSRAM HBO 100/W2) is used to excite the labelled antibodies and 200 milliwatts of the 546 mm band reach disk 14 which has a surface area of $3 \times 10^{-2} cm^2$. The fluorescent signal is $1.4 \times 10^3$ photoelectrons per second when $\epsilon = 2.5 \ 10^{-17} \ cm^2$-molecule$^{-1}$ $N = 3.33 \times 10^5$ molecules-cm$^{-2}$ or $10^4$ molecules in trapping surface $\phi = 0.5$ $\beta = 0.2$ $q = 0.1$ The signal-to-noise ratio can be increased further by operating arc lamp 42 in a pulsed mode and gating photomultiplier tube 56 for the duration of the pulse by means of a controller 66. This eliminates most of the photomultiplier dark noise. The main factor limiting sensitivity is the residual fluorescence of the agarose gel which is minimized by utilizing a fluorescent tag in the red or near IR having a narrow emission band.

This value of N does not necessarily mean that the potential sensitivity of this proposed method is much greater than that of the RIA. The sensitivity of either method is limited not by instrumental detection capabilities but by non-instrumental noise sources, like non-specific interactions which may result in the attachement of tagged antibody molecules to sites other than the antigen under investigation.

In addition, the proposed fluorescent method may introduce two noise sources not present in the RIA, namely, a a residual fluorescence of the antigen-trapping matrix, and photochemical effects produced at high excitation intensities.

Both of these noise sources can, however, be minimized. The residual fluorescence is minimized by using a trapping surface of small area as described previously. If we assume that the main noise component is the residual fluorescence, then the signal-to-noise ratio should be proportional to $A^{-1}$, where A is the area of the trapping surface.

The fluorescence signal, expressed in photo-electrons per second at the photocathode surface is given by $$S = K(\epsilon N)$$

where
K is a constant which includes the fluorescence efficiency, fluorescence collection efficiency, photoelectric quantum efficiency of the photocathode and number of incident photons on the antigen-trapping surface, parameters which are assumed invariant $\epsilon$ is the absorption coefficient of the fluorescent molecules N is the concentration of the fluorescent molecules Now $N = N_T/A$ where $N_T$ is the total number of fluorescent molecules on the trapping suface, and it is assumed to be invariant. Therefore, $$S = K\epsilon N_T/A \quad (1)$$

If we assume that the main contributions to the noise n are the background fluorescence from the trapping surface and the fluctuations in S, we have $$\frac{S}{n} = \frac{K\epsilon N_T A^{-1}}{(K\epsilon N_T A^{-1} + B)^{0.5}} \quad (2)$$

where B is the contribution of the background fluorescence to the photo-electric current. B is independent of the area, since we have assumed an invariant total number of incident photons and an invariant fluorescence collection efficiency, and equation (1) implies that the excitation light intensity is small enough to avoid saturation effects.

Therefore, the area dependence of S/n is determined by which of the two terms in the denominator is dominant. If $K\epsilon N_T A^{-1} >> B$, then S/n is proportional to $A^{-0.5}$. If $B >> K\epsilon N_T A^{-1}$, a situation which is encountered for very small values of $N_T$, Then S/n is proportional to $A^{-1}$.

Both the residual fluorescence and the photochemical effects are minimized with excitation wavelengths in the visible region, instead of ultraviolet. The longer the excitation wavelength, the smaller the number of untagged molecules which can be excited and the lower probability of photochemical changes.

In an alternate embodiment, a fluorescent tag which has a peak absorption wavelength near 632.8 nm (the He-Ne laser wavelength) is used and the fluorescence is measured at longer wavelengths with a photomultiplier having a gallium arsenide photocathode. Some important advantages of using the He-Ne laser for fluorescence excitation are the low cost of the light source, a useful lifetime of thousands of hours, and the saving in optical components (e.g., filters and lenses) which would otherwise be required with non-coherent sources.

In the case of the enzyme-tagged antibodies, the greatly increased sensitivity is obtained when the enzyme substrate does not undergo any appreciable change in the absence of the enzyme, a condition which is not always obtained, but which can be achieved with very small volumes of the substrate solution (another consideration which dictates the use of small antigen-trapping surface areas).

In the preceding examples, each particle of the substance to be measured has a binding reaction with at least two molecules of the specific reagent, namely a molecule of the unlabelled reagent and a molecule of the labelled reagent. An alternate procedure is used within the scope of this invention for measuring a substance whose unit particles react with only one molecule of the specific reagent. In this case, the procedure is essentially the same as in the preceding examples, except that the substance to be analyzed is trapped on the porous base stratum without the intervention of a specific unlabelled reagent. Such trapping is accomplished, for instance, by non-specific physical forces, like entrapment by filtration through a medium with pores smaller than the particles of the substance to be measured, or by non-specific chemical binding. The labelled reagent, however, is specific for the substance to be measured. Otherwise, the specific reagent would attach to substances other than the substance to be measured, thus interfering with the measurement.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A method for measuring minute quantities of a substance comprising the steps of:
   (a) making a fluid containing said substance to be measured flow into contact with a thin porous base stratum of small surface area attached to a solid support, said base stratum containing an immobilized unlabelled reagent having a specific binding reaction with said substance to be measured, said substance to be measured being bound to said immobilized unlabelled reagent;
   (b) immersing said base stratum containing said substance to be measured bound to said immobilized unlabelled reagent into a liquid containing a fluorescent labelled reagent, said labelled reagent attaching to said bound substance to be measured; and
   (c) determining the concentration of said substance to be measured by exciting the fluorescence of said labelled reagent with an excitation light source and measuring the fluorescence intensity emitted by said labelled reagent, said fluorescence intensity being determined by the concentration of said bound substance to be measured.

2. The method as claimed in claim 1 wherein said base stratum has a surface area less than 0.5 cm² and a thickness less than 0.2 cm.

3. The method as claimed in claim 1 wherein said base stratum has a surface area less than 0.1 cm² and a thickness less than 0.1 cm.

4. The method as claimed in claim 2 wherein said immobilized unlabelled reagent is an antibody, said substance to be measured is an antigen and said labelled reagent is essentially said antibody having a fluorescent label, both said unlabelled antibody and said labelled antibody being specific to said antigen.

5. The method as claimed in claim 2 wherein said substance to be measured is capable of immunospecific reactions and is selected from the group consisting of hormones, serum proteins and macromolecules, subcellular particles, viruses, bacteria, whole cells and drugs.

6. The method as claimed in claim 2 wherein said substance to be measured is an antibody, said unlabelled reagent is an antigen specific to said antibody and said labelled reagent is essentially said specific antigen having a fluorescent label.

7. A method for measuring minute quantities of a substance comprising the steps of:
(a) making a fluid containing said substance to be measured flow into contact with a porous base stratum of small surface area attached to a solid support, said base stratum containing an immobilized unlabelled reagent having a specific binding reaction with said substance to be measured, said substance to be measured being bound to said immobilized unlabelled reagent;
(b) immersing said base stratum containing said substance to be measured bound to said immobilized unlabelled reagent into a liquid containing a labelled reagent, said labelled reagent having a bound fluorogenic label, said labelled reagent attaching to said bound substance to be measured;
(c) reacting the fluorogenic label on said labelled reagent with an appropriate substance, thus generating a fluorescent product, the amount of said product being determined by the concentration of said substance to be meaured bound to the immobilized unlabelled reagent; and
(d) determining the concentration of said substance to be measured by exciting said fluorescent product with an excitation light source and measuring the fluorescence intensity emitted by said fluorescent product, said fluorescence intensity being determined by the concentration of said substance to be measured.

8. The method as claimed in claim 7 wherein said base stratum has a surface area less than 0.5 cm² and a thickness less than 0.2 cm.

9. The method as claimed in claim 7 wherein said base stratum has a surface area less than 0.1 cm² and a thickness not greater than 0.1 cm.

10. The method as claimed in claim 7 wherein said substance to be measured is capable of immunospecific reactions and is selected from the group consisting of hormones, serum proteins and macromolecules, subcellular particles, viruses, bacteria, whole cells and drugs.

11. The method as claimed in claim 7 wherein said fluorogenic label is an enzyme.

12. A method for measuring minute quantities of a substance comprising the steps of:
(a) making a fluid containing said substance to be measured flow into contact with a porous base stratum of small surface area attached to a solid support, particles of said substance to be measured being trapped by said base stratum, thus forming a distribution of the substance to be measured on said base stratum;
(b) immersing said base stratum with said distribution of the substance to be measured into a liquid containing a labelled reagent specific for said substance to be measured, such specific reagent containing a fluorescent label, said labelled reagent attaching to said substance to be measured; and
(c) determining the concentration of said substance to be measured by exciting the fluorescence of said flourescent-labelled reagent attached to said substance to be measured with an excitation light source and measuring the fluorescence intensity emitted by said fluorescence-labelled reagent, said fluorescence intensity being determined by the concentration of said substance to be measured.

13. The method as claimed in claim 12 wherein said base stratum has a surface area less than 0.5 cm² and a thickness less than 0.2 cm.

14. The method as claimed in claim 12 wherein said base stratum has a surface area less than 0.1 cm² and a thickness less than 0.1 cm.

15. An apparatus for the fluorometric measurment of minute quantities of a substance in a fluid, said apparatus comprising:
(a) a base stratum of small surface area having the ability to bind and immobilize the substance to be measured, said base stratum attached to a solid support;
(b) means for concentrating the substance to be measured on said base stratum by making said substance to be measured flow into contact with said base stratum, the substance to be measured being bound to said base stratum as it flows into contact therewith;
(c) means for attaching a specific labelled reagent to said substance to be measured bound to said base stratum, the amount of said attached labelled reagent being determined by the amount of the substance to be measured bound to said base stratum, said labelled reagent having a fluorescent label;
(d) an excitation light source for exciting the fluorescence of said labelled reagent; and
(e) means for collecting, detecting and measuring the fluorescence so generated, the intensity of said fluorescence being dependent on the amount of said substance to be measured bound to said base stratum.

16. The apparatus as claimed in claim 5 wherein said base stratum has a surface area less than 0.5 cm² and a thickness not greater than 0.2 cm.

17. The apparatus as claimed in claim 5 wherein said base stratum has a surface area less than 0.1 cm² and a thickness not greater than 0.1 cm.

18. An apparatus for the fluorometric measurement of minute quantities of a substance in a fluid, said apparatus comprising:
(a) a porous base stratum of small surface area having the ability to bind and immobilize the substance to be measured, said base stratum attached to a solid support;

(b) means for concentrating the substance to be measured on said base stratum by making said substance to be measured flow into contact with said base stratum, the substance to be measured being bound to said base stratum as it flows into contact therewith;

(c) means for attaching a specific labelled reagent to said substance to be measured bound to said base stratum, said labelled reagent having a fluorogenic label, the amount of said attached label reagent being determined by the amount of the substance to be measured bound to said base stratum;

(d) means to generate a fluorescent product by reacting said bound fluorogenic labelled reagent with a suitable non-fluorescent compound;

(e) an excitation light source for exciting the fluorescence of said fluorescent product; and (f) means for collecting, detecting and measuring the fluorescence so generated, the intensity of said fluorescence being dependent on the amount of said substance to be measured bound to said base stratum.

19. The apparatus as claimed in claim 18 wherein said base stratum has a surface area less than 0.5 cm$^2$ and a thickness less than 0.2 cm.

20. The apparatus as claimed in claim 18 wherein said base stratum has a surface area less than 0.1 cm$^2$ and a thickness less than 0.1 cm.

21. The apparatus as claimed in claim 18 wherein said fluorogenic label is an enzyme.

22. A device for immobilizing minute quantities of a substance present in a fluid, said device comprising:

(a) a porous base stratum of small surface area attached to a solid support; and (b) an unlabelled reagent immobilized on said base stratum, said reagent having the ability to bind and immobilize said substance present in said fluid.

23. The device as claimed in claim 22 wherein said base stratum has a surface area less than 0.5 cm$^2$ and a thickness less than 0.2 cm.

24. The device as claimed in claim 22 wherein said base stratum has a surface area less than 0.1 cm$^2$ and a thickness less and 0.1 cm.

* * * * *

UNITED STATES PATENT OFFICE
CERTIFICATE OF CORRECTION

PATENT NO. : 4,153,675
DATED : May 8, 1979
INVENTOR(S) : Marcos Kleinerman

It is certified that error appears in the above-identified patent and that said Letters Patent are hereby corrected as shown below:

On the cover page at the heading "Notice" change "The portion of the term of this patent subsequent to Jul. 19, 1974, has been disclaimed." to -- The portion of the term of this patent subsequent to Jul. 19, 1994, has been disclaimed.--

Signed and Sealed this

Twenty-third Day of October 1979

[SEAL]

Attest:

RUTH C. MASON
Attesting Officer

LUTRELLE F. PARKER
Acting Commissioner of Patents and Trademarks